Figure 1:
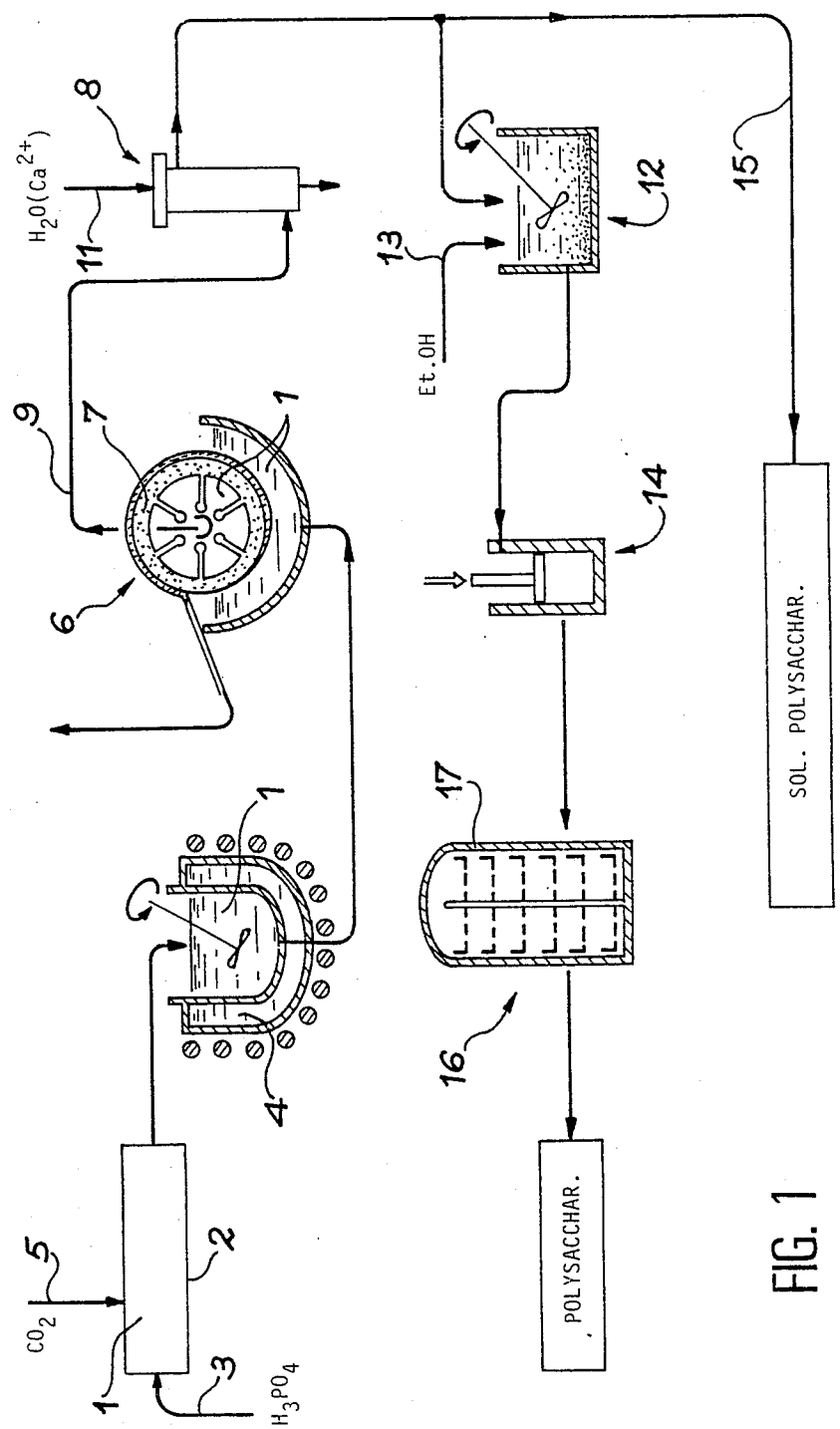

United States Patent [19]

Barnier et al.

[11] Patent Number: 4,906,746
[45] Date of Patent: Mar. 6, 1990

[54] PROCESS FOR THE PRODUCTION AND EXTRACTION OF POLYSACCHARIDES FROM A PORPHYRIDIUM CRUENTUM CULTURE AND APPARATUS FOR PERFORMING THE PROCESS

[75] Inventors: Henri Barnier, Aix en Provence; Patrick F. Ferreira Dos Santos, Venelles; Claude Gudin, Aix en Provence; Catherine Thepenier, Manosque, all of France

[73] Assignee: Commissariat a l'Energie Atomique, Paris, France

[21] Appl. No.: 249,594

[22] Filed: Sep. 26, 1988

[30] Foreign Application Priority Data

Oct. 6, 1987 [FR] France .................. 87 13780

[51] Int. Cl.$^4$ .................. C07H 1/06; C07G 17/00; C12P 19/04; C12P 19/44
[52] U.S. Cl. .................. 536/127; 536/124; 435/72; 435/74; 435/101; 435/100
[58] Field of Search .................. 536/127, 124; 435/72, 435/74, 101, 100

[56] References Cited

U.S. PATENT DOCUMENTS 4,087,936  5/1978  Savins et al. .................. 47/1.4
4,417,415  11/1983 Cysewski et al. .................. 47/1.4

OTHER PUBLICATIONS

A Process for the Production of Polysaccharides from Microalga, Daniel B. Anderson et al., Biotechnology and Bioengineering Symp. No. 15 (1985) pp. 533–547.

Primary Examiner—Ronald W. Griffin
Assistant Examiner—Everett White
Attorney, Agent, or Firm—Pearne, Gordon, McCoy & Granger

[57] ABSTRACT

Process for the production and extraction of polysaccharides from a porphyridium cruentum culture and apparatus for performing the process.

This production and extraction process comprises a stage of concentrating the polysaccharides consisting of leaving the culture medium (1) in a photoreactor (22) exposed to sunlight under stagnant conditions and at ambient temperature, leading to the formation of a polysaccharide-rich cream (23) and recovering said cream by skimming, a stage (24) of heating the concentrate obtained at a temperature between 60° and 100° C., a stage of separating the solid and liquid phases formed (26), a stage (30) of precipitating the polysaccharides contained in the liquid phase and a stage (16) of drying the precipitate obtained.

19 Claims, 2 Drawing Sheets

PROCESS FOR THE PRODUCTION AND EXTRACTION OF POLYSACCHARIDES FROM A PORPHYRIDIUM CRUENTUM CULTURE AND APPARATUS FOR PERFORMING THE PROCESS

DESCRIPTION

The present invention relates to a process for the production and extraction of polysaccharides from a culture of microalgae in a solar photobioreactor, as well as to the photobioreactor for performing the process. The microalga studied is porphyridium cruentum, which excretes polysaccharides forming a waste deposit or gangue around the cellular membrane, whose thickness varies with the age of the cell.

Porphyridium cruentum produces polysaccharides of three types, namely intracellular polysaccharides, pericellular polysaccharides and hydrosolubilized polysaccharides. These three polysaccharide types have a molecular weight exceeding 1,000,000 Dalton and can rise even to 4,000,000 Dalton, whilst having the same base products, namely sugars, sulphates and uronic acids. The sugars are mainly glucose, galactose and xylose.

The proportion of each of these base products in the three polysaccharide types is not known. The rheological characteristics are identical for pericellular and hydrosolubilized polysaccharides and are unknown for intracellular polysaccharides.

The inventive process relates to the production and extraction of hydrosolubilized polysaccharides alone, as well as to the simultaneous production and extraction of the three polysaccharide types.

The invention advantageously applies to the agro-alimentary field and to that of oil extraction. In the agro-alimentary field, the polysaccharides are used as additives for modifying the viscosity of an aqueous or milky medium and are more particularly used in pork butchery or ice creams. In the oil sector, polysaccharides are used as surfactants for modifying the ratio of the forces with the storage rock and thus making it possible to extract oil from the rock.

U.S. patent application Ser. No. 3,195,271 discloses the artificial culturing of porphyridium cruentum for producing polysaccharides. The process described in this patent recommends the addition of alcohol to the microalga culture, whereof the alcohol volume/culture volume is equal to 1, in order to form a coagulum. The alcohol-treated culture volume is directly removed from the solar cultivator without undergoing a concentration stage. Moreover, this process does not provide for the extraction or purification of polysaccharides, or for the recovery of the microalgae or biomass with a view to a further polysaccharide production.

U.S. patent application Ser. No. 4,417,415 relates to a process for the production and extraction of polysaccharides from porphyridium cruentum and deals with the recovery of total polysaccharides, i.e. intracellular, pericellular and exocellular polysaccharides. It involves a concentration stage by ultrafiltration, followed by hot basification of the concentrate with soda and then cold acidification with hydrochloric acid. This hydrolysis is followed by filtration and then a first precipitation with ethanol using 2 to 3 ethanol volumes per filtrate volume.

The precipitate obtained is then redissolved in a calcium chloride solution. A second precipitation with ethanol with 3 volumes of ethanol per solution volume is then carried out. This second precipitate essentially constituted by polysaccharides is dried and then ground.

This process necessarily involves the destruction of the biomass and consequently the production of a new biomass for each polysaccharide production cycle. Apart from the destruction of the biomass, it suffers from the further disadvantage of being long and tedious to carry out. In addition, the alcohol quantities used are very significant leading to a long and costly drying. Furthermore, the filtrates treated by soda and hydrochloric acid are not very highly concentrated in polysaccharides and the necessary quantities of these two products are high, which further increases the costs of the process.

A similar process for the production and extraction of total polysaccharides by culture of porphyridium cruentum also using a concentration stage followed by hot basification and then acidification is described in Biotechnology and Bioengineering Symp. No. 15, 1985, pp. 533–547 by D. B. Anderson et al "A process for the production of polysaccharides from microalgae".

Other processes, like that described in U.S. patent application Ser. No. 4,087,936, relate to the production of total biopolymers produced by porphyridium aerugineum, where once again the biomass is destroyed.

The present invention relates to a process for the production and extraction of polysaccharides produced by porphyridium cruentum which is relatively simple and inexpensive, whilst the biomass is recovered and valorized.

More specifically the invention relates to a process for the production and extraction of polysaccharides from a culture of the microalga porphyridium cruentum involving a stage or step of concentrating polysaccharides produced by the microalga, a stage of heating to a temperature from 60° to 100° C., a stage of precipitating polysaccharides in solution and a stage of drying the precipitate obtained.

The inventive process, unlike those described in U.S. patent application Ser. No. 4,417,415 and the article by B. D. Anderson, only relates to pericellular and exocellular polysaccharides, i.e. the polysaccharides excreted by the microalga and forming a gangue around the cellular membrane. These polysaccharides represent 70 to 75% of the total polysaccharides, which is very adequate and does not justify the long and costly prior art processes for extracting all the polysaccharides, including those present in the microalgae.

Thus, the solid phase containing the microalgae can be recycled with a view to a further production and extraction of polysaccharides, unlike in the case of the prior art. In addition, the inventive process advantageously comprises a stage of separating the solid and liquid phases present. Moreover, it does not involve a basification or a neutralization stage.

To this end, the inventive process essentially comprises the concentration of the pericellular and exocellular polysaccharides produced by the microalga, heating, the separation of the solid and liquid phases present, the precipitation of the polysaccharides present in the liquid phase, a pressing of the polysaccharide precipitate and the drying of the pressed precipitate.

The heating stage according to the invention makes it possible to increase by at least 18% the precipitatable materials and this can even rise to 50%, which leads to a rise of at least 30% in the extracted and purified polysaccharides, (which can even be up to 80%) compared with a process involving no such heating stage. Thus, this stage permits a partial solubilization of the polysaccharides of the gangue produced by the microalga.

Preferably the heating stage is performed at approximately 80° C. and heating lasts between 30 and 60 minutes.

According to the invention, the precipitation stage can be performed before or after the concentration stage and this also applies with respect to the precipitate drying stage.

Moreover, the heating stage can be performed before or after the concentration stage. It can also be carried out before or after the stage of separating the solid and liquid phases. The order of the stages of the process is dependent on the nature of the stages.

The precipitation of the polysaccharides according to the invention can be carried out with cetyl pyridinium chloride or CPC, said precipitation by a quaternary ammonium salt being rendered possible as a result of the polyanionic character ($COO^-$ and $SO_3^-$ grouping) of the polysaccharides.

The addition of an adequate CPC quantity to the polysaccharide solution leads to the formation of a precipitate with a fixed composition and formed by 55% polysaccharides and 45% CPC. This precipitation method permits a concentration of the polysaccharides by a factor exceeding 5.

In view of the existing difficulties in completely eliminating the residual ammonium, the precipitation of the polysaccharides present in the liquid phase is preferably carried out by the addition of alcohol in a ratio R of the alcohol volume to the liquid phase volume just prior to the addition of the alcohol at the most equal to 1 and in particular between 0.5 and 1.

With the process of the invention, it is possible to extract more than 90% of the organic matter contained in the liquid phase whilst only using 50% by volume of alcohol, which corresponds to a ratio equal to 1.

This precipitation method, although less selective than that by CPC, the quantity of material collected or harvested by CPC only representing 40% of the organic materials precipitated by the alcohol, is much simpler than precipitation by CPC.

Precipitation by alcohol is accompanied by a saline coprecipitation, the precipitate obtained containing 70 to 80% salts.

The mass of precipitates obtained is 5 to 10% higher when the alcohol addition is fast compared with a slow addition. Moreover, these precipitates contain no more than 40% of salts after six washing operations in hydroalcoholic mixtures.

The alcohols usable in the invention are primary, secondary or tertiary alcohols with 1 to 3 carbon atoms. Usable alcohols are methanol, ethanol, isopropanol, n-propanol and a mixture thereof.

According to the invention, the stage of concentrating the polysaccharides is carried out either by skimming, or by ultrafiltration, optionally associated with diafiltration.

The collection or harvesting by skimming of the exocellular polysaccharides is carried out by transferring the culture at the end of the culture cycle in a photobioreactor which is exposed to sunlight, under stagnant conditions, leading to the surface formation of a polysaccharide-rich cream, which is collected by skimming.

On analysis, the creamy concentrate obtained is found to be rich in polysaccharides, the content being well above that of the underlying culture. Following the removal of said concentrate, it is reconstituted during the following hours.

The formation of the creamy concentrate is a surface phenomenon. Thus, no evolution of the viscosity or of the polysaccharide content is revealed in the underlying culture and this applies no matter what the volume of said culture.

The cream has an appearance of a thick, viscous film containing 5 to 40 g/L of hydrosolubilized polysaccharides, which compared with the underlying culture represents a concentration factor of 10 to 60 of the hydrosolubilized polysaccharide content. It contains the three polysaccharide types defined hereinbefore.

Through the solubilization thereof in water heated to between 60° and 100° C., a uniformly dispersed concentrated solution is obtained. The collection of the hydrosolubilized polysaccharides, by separation of the solid and liquid phases by centrifuging or filtration, requires a prior dilution of said solution.

The "motor" of said cream is sunlight. Moreover, this phenomenon can be assisted by maintaining the photobioreactor at a temperature between 10° and 40° C., the culture medium being present in the photobioreactor for between 12 and 72 and preferably 24 and 48 hours. Moreover, the cream quantity is linked with the surface/volume ratio of the photobioreactor. Moreover, the latter is advantageously in the form of a "flat" dish or tank, whereof the surface/volume ratio is at least equal to 10 $m^{-1}$ with a minimum height of 10 cm.

The concentration of the polysaccharides can also be brought about by ultrafiltration, preferably associated with diafiltration.

Ultrafiltration or diafiltration is carried out in the conventional way. During diafiltration the liquid introduced is either water which corresponds to a simple diafiltration, or a previously defined salinity medium, which corresponds to a diafiltration with an ionic balance change.

The concentrates obtained have the same rheological characteristics as native solutions (pseudo-plasticity, flow threshold, limited sensitivity to salts) and their viscosity is well above that of native solutions.

Diafiltration, which is particularly associated with ultrafiltration, serves to reduce the total saline charge of the concentrates either by retaining the same proportions of salts, or by modifying the saline composition, i.e. by exchanging $Ca^{++}$ ions with $Na^+$ ions.

The modification of the $Na^+/Ca^{++}$ ratio (by eliminating the $Na^+$ ions) makes it possible to precipitate all the polysaccharides in calcium form by the method of alcoholic precipitation with an alcohol rate of 40 to 50% by volume only, which corresponds to a ratio R of the volumes of 0.67 to 1.

Compared with the previously described skimming method, this concentration method produces with ultrafiltration, diafiltration or dialysis membranes, whereof the cutoff zone is between 12,000 and 110,000, leads to small modifications to the polysaccharide solutions corresponding to a 0 to 20% by weight loss of polysaccharides sometimes accompanied by a viscosity drop.

Moreover, it should be noted that a small residual content of salts affects the characteristics of the polysaccharides during the drying stage. In particular, for equal concentration, the polysaccharides dried before dialysis have viscosities well above those of polysaccharides dried after dialysis.

The redissolving of dried polysaccharides prior to dialysis is easier, which can be advantageous for their use as a rheology modification additive in connection with the viscosity of a liquid medium, particularly in the agro-alimentary field.

According to the invention, the separation of the solid and liquid phases present can be carried out by centrifuging between 5,000 and 40,000 g and preferably 20,000 and 35,000 g, provided that the viscosity of the starting medium does not exceed 700 to 800 cPo (at 1.8 per second) and that said centrifuging is carried out in the hours following the stopping of the culture.

Moreover, the viscosity of the centrifugates decreases a little with the increase in the number of g, which corresponds to the elimination of a small part of the polysaccharides.

It is possible to carry out the separation stage of the solid and liquid phases by vacuum filtration. The separation of the cultures on rotary filters with pre-layers of diatoms (or micro-algae) makes it possible to obtain a clear filtrate with a flow rate between 100 and 400 L/h/m$^2$.

This solid/liquid separation method, although quite satisfactory, makes it possible to obtain a polysaccharide content lower than that of the centrifuging method. A maximum difference of 30% on the total polysaccharide content can be observed.

The heating of the culture according to the invention prior to this filtration stage makes it possible to increase to 30% the polysaccharide content of the filtrate, which is due to the fact that part of the polysaccharides of the gangue dissolves during heating.

According to the invention, the drying of the polysaccharides takes place for 12 to 72 hours and for e.g. 24 to 48 hours at a temperature between 30° and 60° C., whilst in particular maintaining a residual humidity level of at least 5% in a ventilated atmosphere.

Other features and advantages of the invention can be better gathered from the following description given in a purely illustrative and non-limitative manner with reference to the drawings, wherein show:

FIG. 1 diagrammatically the different stages of the extraction process according to the invention of hydrosolubilized polysaccharides from a porphyridium cruentum culture.

Figure 2:
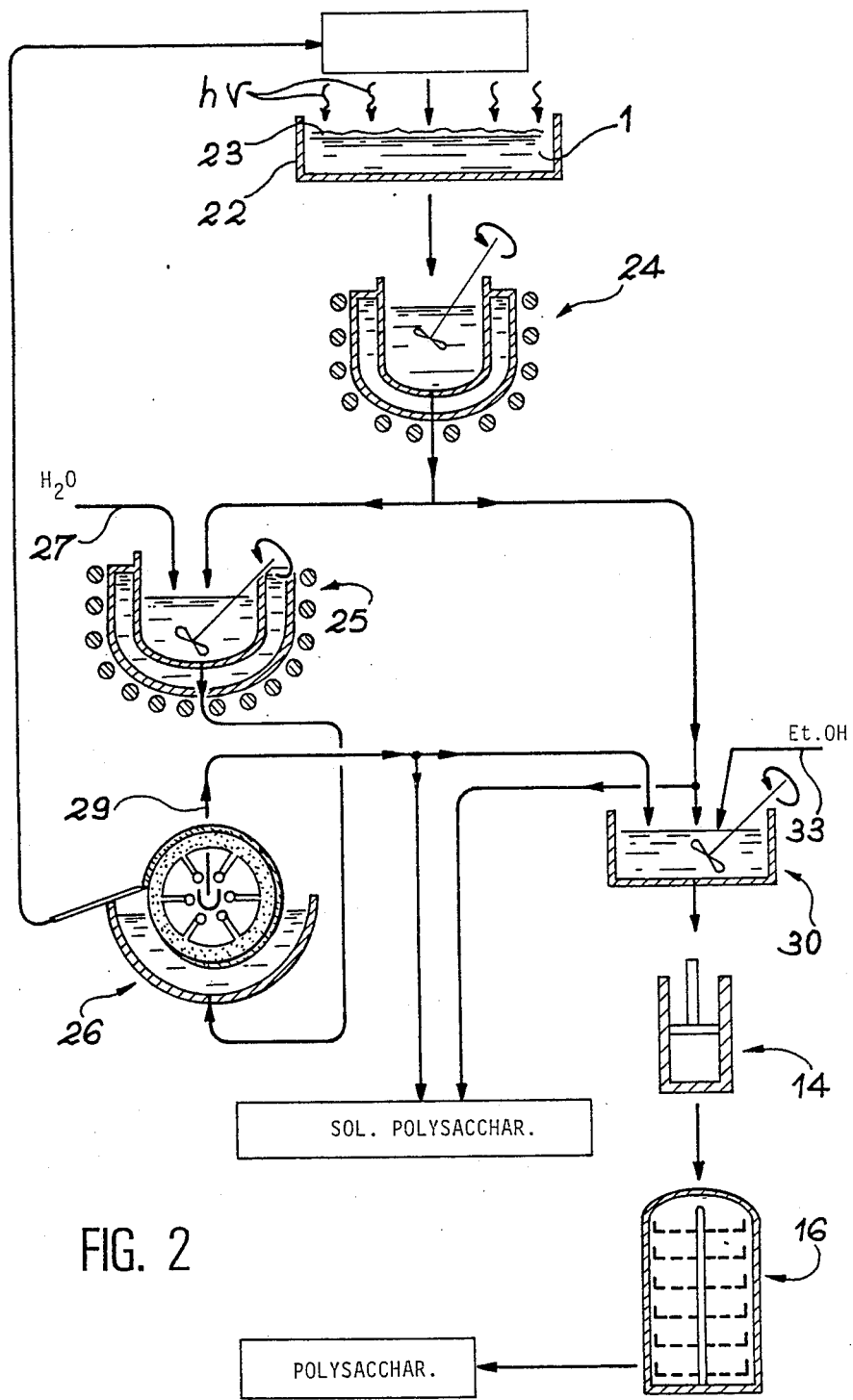

FIG. 2 diagrammatically the different stages of the inventive process for the recovery of pericellular and exocellular polysaccharides produced by a porphyridium cruentum culture.

As shown in FIG. 1, the porphyridium cruentum culture 1 is produced in an approximately 10 m$^3$ photobioreactor 2 containing as the nutrient medium synthetic seawater enriched with potassium, phosphorus and nitrogen. The potassium is present in the form of chloride, the phosphorus in the form of orthophosphoric acid and the nitrogen in the form of urea. The pH of the culture medium is regulated to between 6 and 8, as indicated at 3 throughout the growth of the microalgae, which lasts approximately 15 days, through the use of orthophosphoric acid. The carbon supply for these microalgae is provided in the form of carbon dioxide, as indicated at 5.

The photobioreactor 2 used is in particular that described in the article by C. Gudin and C. Thepenier "Bioconversion of solar energy into organic chemicals by microalgae" published in Advances in Biotechnological Processes 6, pp. 73-110, 1986.

Culture 1 is then placed in a water bath 4 heated to 80° C. for 30 to 60 minutes and accompanied by stirring. There is then no further pH regulation and in addition the $CO_2$ supply is stopped.

As indicated at 6, the culture 1 is then filtered on a rotary filter 7 with pre-layers of diatoms and at a flow rate of approximately 300 L/h/m$^2$ and the diatom/algae ratio of the filter cake is close to 13 for a filter of 0.1 m$^2$. A non-optimized test on a 1.9 m$^2$ filter gave a ratio of 3.3.

The clear filtrate 9 obtained at 6 and containing 70 to 75% by weight of total polysaccharides of the culture is then concentrated, as indicated at 8, whilst the residue obtained in 6 and containing the cellular biomass, i.e. porphyridium cruentum micro-algae can then be recovered and treated for the extraction of other products.

The concentration in 8 of the polysaccharide-rich filtrate is carried out by ultrafiltration associated with diafiltration using a mineral membrane with a pore radius of 2 to 50 nm. In the latter case, the water circulating tangentially to the membrane, as indicated at 11, contains calcium chloride in order to exchange the $Na^+$ ions of the polysaccharide solution with $Ca^{++}$ ions. As a function of the particular case, volume concentration factors of 10 can be obtained during ultrafiltration.

The filtrate obtained at 8 is then precipitated, as indicated at 12, with ethanol supplied at 13. The alcohol volume/filtrate volume ratio R is equal to 1.0.

More than 95% of the hydrosolubilized polysaccharides contained in the filtrate from 8 are then precipitated.

It is also possible to use the residue obtained in 6, following an adequate treatment in e.g. pisciculture for feeding fish and molluscs.

The polysaccharide precipitate obtained in 12 then undergoes pressing, as indicated at 14.

The pressed product is then dried, as indicated at 16, in a column 17 heated to 40° C. in the presence of air for 48 hours and whilst maintaining a residual humidity of at least approximately 5%. The dried product obtained only contains the polysaccharides which were hydrosolubilized.

FIG. 2 diagrammatically shows the different stages of the recovery of pericellular and exocellular polysaccharides produced by a porphyridium cruentum culture. The culture 1, carried out under the same operating conditions as those described relative to FIG. 1, is firstly transferred into a parallelepipedic "flat" tank 22, whereof the base to volume surface ratio is $\geq 10m^{-1}$ and whose height is $\geq 10cm$.

This tank 22 is not stirred, not covered and left under natural light intensity and temperature conditions (corresponding to a mean light intensity of 4000 kcal/m$^2$/day and a temperature of 20° to 40° C.) for 24 hours. There is then no further regulation of the pH of the culture and $CO_2$ supply is stopped.

A cream 23 rich in pericellular and exocellular polysaccharides then forms (5 to 40 g/L of polysaccharides). The cream formed can be collected every 24 hours. The collected creamy product 23 is then heated in a water bath, as illustrated at 24, at a temperature of 80° C. for 1 hour, heating being accompanied by stirring.

Following heating of the creamy concentrate and an appropriate dilution, as indicated at 25, the latter can be filtered on a rotary filter with pre-layers of diatoms, as indicated at 26 and in the same way as described hereinbefore, with a view to obtaining polysaccharides produced by porphyridium cruentum. This vacuum filtration 26 requires a prior dilution of the creamy concentrate, as shown at 25 in the drawing.

It is also possible to carry out the separation of the solid and liquid phases formed, following the heating stage 24, by centrifuging at between 20,000 and 35,000 g.

The centrifugate or the filtrate 29 obtained at 26 is then precipitated as indicated at 30 with ethanol arriving at 33. The ratio of the ethanol volume to the volume of the filtrate 29 or that of the centrifugate is equal to 1.0.

The solid phase obtained at 26 is recycled with a view to the extraction of other products (starch, lipids, etc.), said solid phase containing most of the microalgae.

It is possible to use the residual culture beneath the cream 23 in pisciculture for feeding fish, crustaceans, etc.

The polysaccharide precipitate obtained at 30 is then, as hereinbefore and under the same conditions, pressed and then dried. The dry product obtained contains the polysaccharides.

Examples illustrating the process for the production and extraction of polysaccharides produced by porphyridium cruentum according to the invention will now be given.

EXAMPLE 1

29 l of a porphyridium cruentum culture containing 0.7 g/L of polysaccharides having undergone no concentration stage, were heated at 80° C. for 1 hour and then filtered at a flow rate of 60 L/h/m². The filtrate obtained contains 2.97 g/L of culture of materials precipitatable with alcohol (and in particular ethanol), i.e. 85.8% of total precipitatable materials, including 0.9 g/L of purified polysaccharides.

COMPARATIVE EXAMPLE 1

46 l of the same culture as in Example 1, but which has undergone no concentration stage were filtered at a flow rate of 104 L/h/m². The filtrate obtained contains 2.51 g/l of culture of materials precipitatable with alcohol (particularly ethanol), i.e. 77.5% of total precipitatable materials. These materials contain 0.7 g/L of pressed and dried, purified polysaccharides.

On comparing Example 1 and comparative Example 1, it is clear that the prior treatment of the culture at 80° C. in this particular case permits an increase of alcohol-precipitatable materials in the filtrate of 18% and an increase of 30% as regards the extracted purified polysaccharides. This clearly indicates the important part played by the heating stage according to the invention prior to the precipitation by alcohol of the polysaccharides.

Alcohol-precipitatable materials are all dissolved materials precipitated with alcohol. These materials more particularly correspond to polysaccharides produced by the microalga and to part of the salts present in the medium.

EXAMPLE 2

On a synthetic seawater medium containing 0.6 g/L of urea and 0.75 g/L of potassium chloride were cultured in a photobioreactor, like that described in the aforementioned Gudin article, porphyridium cruentum microalgae for 10 days. The pH was regulated to 6.0 with orthophosphoric acid and the carbon supply to the micro-algae was in the form of carbon dioxide at a mean flow rate of 100 L/h/m³ of culture. The culture temperature was 20° to 30° C. and the mean illumination 4000 kcal/m²/day.

The culture obtained was then placed in a parallelepipedic tank with a height of 10 cm and a base surface of 10 m², a length of 10 m and a width of 1 m. The culture was maintained under stagnant conditions (unstirred and uncovered tank) for 24 hours, without regulating the pH, or supplying $CO_2$, whilst modifying the temperature of the culture and its lighting. The results obtained are given in Table I.

TABLE I

| Illumination | Temperature | Creaming |
| --- | --- | --- |
| Darkness | 15° C. | No cream |
| " | 35° C. | " |
| Artificial light* | 15° C. | Cream |
| " | 35° C. | More intense cream |

*Artificial light with an intensity of 400 kcal/m²/day.

Table I clearly shows the importance of light and a temperature at least equal to 10° C. for obtaining the creaming phenomenon. A temperature above 40° C. leads to a partial destruction of the culture or to an inhibition of the production of polysaccharides by microalgae. In the same way, a temperature below 10° C. inhibits the creaming phenomenon.

Using the aforementioned tank with a surface area of 10 m², in natural light and at approximately 30° C., it was possible to extract in three skimming operations (staggered over a week) 80% of the hydrosolubilized polysaccharides present in only 2% of the culture volume placed in the tank.

EXAMPLE 3

1000 litres of a porphyridium cruentum culture containing 0.25 g/L of polysaccharides at the end of the culture cycle are spread over a flat tank with a base surface/volume ratio of 10. After exposure for 24 hours under stagnant natural conditions (sunlight and ambient temperature), 11 litres of cream containing 5.34 g/L of polysaccharides are collected, which represents a mass concentration factor of 21.

This cream was then appropriately diluted in water, heated for 1 hour at 80° C. accompanied by stirring and then centrifuged at 20,000 g. The supernatant matter obtained contains 8.0 g/L of polysaccharides, which represents an increase of 50% in the polysaccharide content compared with the content obtained before the heating stage.

The polysaccharides present in the liquid phase are then precipitated by the addition of ethanol with equal volume. The precipitate is pressed and dried at 40° C. in a ventilated atmosphere for 48 hours.

EXAMPLE 4

1.5 m³ of a porphyridium cruentum culture containing 0.21 g/L of polysaccharides at the end of the culture cycle are spread over a flat tank with a surface/volume ratio equal to 11.3. Following 48 hours exposure under natural, stagnant conditions 10.3 L of cream containing 6.8 g/L of polysaccharides were obtained, which represents a mass concentration factor of 32.

The cream obtained is then appropriately diluted in water, heated for 1 hour at 80° C. accompanied by stirring and then centrifuged at 20,000 g. The supernatant matter obtained contains 9.0 g/L of polysaccharides, giving a mass concentration factor of 43 instead of 32 before the heating stage.

The polysaccharides collected are then precipitated by the addition of ethanol in equal volume. This precipitate is then pressed and dried at 40° C. in a ventilated atmosphere for 48 hours.

EXAMPLE 5 to 7

1.5 m³ of a porphyridium cruentum culture containing 0.21 g/L of polysaccharides at the end of the culture cycle are spread over a flat tank with a base surface/volume ratio equal to 11.3. After variable exposure times under natural, stagnant conditions, the cream formed is appropriately diluted in water, heated for 1 hour at 80° C. and then centrifuged at 20,000 g. The supernatant matter obtained is then precipitated by the addition of 1 volume of ethanol. The precipitate obtained is pressed and then dried at 40° C. in a ventilated atmosphere and for 48 hours. The results obtained are given in Table II.

TABLE II

| Ex. | Standing time before collecting the cream (days) | Recovered creamy concentrate volume (L) | Polysaccharide concentration in the creamy concentrate (g/L) | Concentration factor | Collection yield (% exocellular polysaccharides) |
|---|---|---|---|---|---|
| 5 | 3 | 15 | 9.1 | 43 | 43.5 |
| 6 | 2 | 10.3 | 9 | 43 | 29.5 |
| 7 | 1 | 7.0 | 5 | 24 | 11 |

Table II clearly indicates that the polysaccharide-rich cream quantity and therefore the polysaccharide quantity increases with the exposure time of the initial culture to sunlight under natural, stagnant conditions.

COMPARATIVE EXAMPLES 2 to 4

5 m³ of a porphyridium cruentum culture containing 0.65 g/L of polysaccharides at the end of the culture cycle were spread over a tank with a base surface/volume ratio equal to 0.70. The culture was maintained under natural, stagnant conditions for variable periods. The cream obtained was then appropriately diluted in water, heated for 1 hour at 80° C. and then centrifuged at 20,000 g. The supernatant matter obtained was precipitated by ethanol at equal volume, then pressed and finally dried at 40° C. in a ventilated atmosphere for 48 hours. The results are given in the following Table III.

TABLE III

| Comparative Ex. | Standing time before collecting the cream (days) | Recovered creamy concentrate volume (L) | Polysaccharide concentration in the creamy concentrate (g/L) | Concentration factor | Collection yield (% exocellular polysaccharides) |
|---|---|---|---|---|---|
| 2 | 4 | 7 | 5.83 | 9 | 1.3 |
| 3 | 2 | 3.2 | 12.3 | 19 | 1.2 |
| 4 | 1 | 2.1 | 8.05 | 12.5 | 0.5 |

Table III clearly shows that the longer the exposure time of the culture under natural conditions, the larger the polysaccharide quantity produced. However, exposure for more than 4 days does not make it possible to significantly increase the production yield.

Moreover, the comparison of comparative Examples 2 to 4 with Examples 5 to 7 clearly indicates the importance played with respect to the creaming phenomenon and therefore the polysaccharide production of the surface/volume ratio of the tank exposed to sunlight under natural, stagnant conditions.

Thus, for a ratio of 0.7, the yield is equal to 1.3 at the end of 4 days of exposure, whilst it is equal to 43.5 at the end of 3 days with a ratio of 11.3.

EXAMPLE 8

A porphyridium cruentum culture containing 0.21 g/L of polysaccharides at the end of the culture cycle was spread over a flat tank with a surface/volume ratio equal to 7 for 6 days, under stagnant, natural conditions as regards sunlight exposure and temperature. The cream obtained was then appropriately diluted in water, heated for 1 hour at 80° C. and then centrifuged at 20,000 g. The supernatant matter obtained was precipitated by the addition of an equal volume of ethanol. The precipitate was pressed and then dried at 40° C. in a ventilated atmosphere for 48 hours.

COMPARATIVE EXAMPLE 5

A porphyridium cruentum culture containing 0.65 g/L of polysaccharides at the end culture cycle was spread over a tank with a surface/volume ratio equal to 0.6 for 7 days under natural, stagnant conditions. The cream obtained was treated under the same conditions as in Example 8. The results are given in Table IV.

TABLE IV

| Comparative | Total recovered creamy concentrate volume (l) | Polysaccharide concentration of the cream (g/l) | concentration factor | Total collection yield (% exocellular polysaccharides) |
|---|---|---|---|---|
| Example 4 | 12.3 | 8.13 | 12.5 | 3 |
| Example 7 | 32.3 | 8.28 | 39 | 84 |

The comparison of Example 8 and comparative Example 5 shows the importance played by the surface/volume ratio of the tank on the production of polysaccharide-rich cream.

We claim:

1. Process for producing and extracting polysaccharides from a culture of the microalga porphyridium cruentum comprising the steps of concentrating pericellular and exocellular polysaccharides produced by the microalga, heating the microalga to a temperature in the range of from 60° to 100° C., separating solid and liquid phases present for recycling microalga in the solid phase without a prior basification or neutralization step for recovery of intracellular polysaccharides, precipitating the polysaccharides present in the liquid phase, and drying the resulting precipitate.

2. Process according to claim 1, including the step of pressing the precipitate prior to drying the precipitate.

3. Process according to claim 2, where the separating step includes centrifuging the solid and liquid phases at between 5,000 and 40,000 g.

4. Process according to claim 2, wherein the separating step includes vacuum filtration of the solid and liquid phases.

5. Process according to claim 1, wherein the step of precipitating the polysaccharides includes adding alcohol to the liquid phase in an alcohol volume/solution volume ratio at most equal to 1.

6. Process according to claim 5, wherein the alcohol volume/solution volume ratio is between 0.5 and 1.

7. Process according to claim 1, wherein the step of heating is performed at a temperature of about 80° C.

8. Process according to claim 1, wherein the step of concentrating the polysaccharides includes forming a polysaccharide-rich cream by exposing the culture to sunlight under stagnant conditions in a photoreactor and recovering said cream by skimming.

9. Process according to claim 8, wherein the step of forming said polysaccharide-rich cream includes maintaining said culture in said photoreactor at a temperature between 10° and 40° C. for 12 to 72 hours.

10. Process according to claim 8, including the step of solubilizing said polysaccharide-rich cream prior to the precipitating step.

11. Process according to claim 8, wherein said photoreactor comprises a flat tank having a surface/volume ratio at least equal to 10 and a thickness at least equal to 10 cm.

12. Process according to claim 1, wherein the concentrating step includes forming a cream rich in pericellular and exocellular polysaccharide by exposing the culture to sunlight under stagnant conditions in a photoreactor, recovering the cream by skimming to form a creamy concentrate, the heating step includes heating the creamy concentrate, the separating step includes separating liquid and solid phases of the creamy concentrate, the precipitating step includes precipitating the polysaccharides present in the liquid phase, and pressing the polysaccharide precipitate prior to the drying step.

13. Process according to claim 12, wherein said photoreactor comprises a flat tank having a surface/volume ratio at least equal to 10 and a thickness at least equal to 10 cm.

14. Process according to claim 1, wherein the step of concentrating the polysaccharides comprises an ultrafiltration step.

15. Process according to claim 14, wherein the concentrating step includes ultrafiltration associated with diafiltration.

16. Process according to claim 1, wherein the heating step includes heating the culture of the microalga, the separating step includes separating solid and liquid phases of the heated culture, the concentrating step includes concentrating the pericellular and exocellular polysaccharides present in the liquid phase by ultrafiltration, the precipitating step includes precipitating the polysaccharides present in the filtrate and pressing the polysaccharide precipitate prior to the drying step.

17. Process according to claim 16, wherein said ultrafiltration is associated with diafiltration.

18. Process according to claim 1, wherein the drying step includes drying the precipitate in a ventilated atmosphere at a temperature between 30° and 60° C.

19. Process according to claim 1, wherein the drying step is carried out at a residual humidity of at least 5%.

* * * * *